United States Patent [19]

Christy

[11] Patent Number: 5,766,217
[45] Date of Patent: Jun. 16, 1998

[54] SURGICAL LOOP DELIVERY DEVICE AND METHOD

[76] Inventor: William J. Christy, 1325 Sunset Dr., Winter Park, Fla. 32789

[21] Appl. No.: 717,990

[22] Filed: Sep. 23, 1996

[51] Int. Cl.⁶ ..................................................... A61B 17/04
[52] U.S. Cl. ........................... 606/148; 606/139; 606/144
[58] Field of Search .................................. 606/139, 144, 606/148, 181, 182, 187, 147, 167, 170

[56] References Cited

U.S. PATENT DOCUMENTS

| | | | |
|---|---|---|---|
| 5,217,471 | 6/1993 | Burkhart | 606/148 |
| 5,242,459 | 9/1993 | Buelna | 606/148 |
| 5,318,578 | 6/1994 | Hasson | 606/139 |
| 5,320,629 | 6/1994 | Noda et al. | 606/139 |
| 5,330,491 | 7/1994 | Walker et al. | 606/148 |
| 5,336,231 | 8/1994 | Adair | 606/148 |
| 5,391,176 | 2/1995 | De La Torre | 606/148 |
| 5,405,351 | 4/1995 | Kinet et al. | 606/139 |
| 5,423,837 | 6/1995 | Mericle et al. | 606/148 |
| 5,454,820 | 10/1995 | Kammerer et al. | 606/148 |
| 5,486,186 | 1/1996 | Yoon | 606/148 |
| 5,571,120 | 11/1996 | Yoon | 606/148 |
| 5,643,293 | 7/1997 | Kogasaka et al. | 606/148 |

*Primary Examiner*—Gary Jackson
*Attorney, Agent, or Firm*—Allen, Dyer, Doppelt, Milbrath & Gilchrist, P.A.

[57] ABSTRACT

A device for delivering a loop of suture material for use in endoscopic ligation is described. The device has a pair of coaxial slidable cylindrical tubes. The outer tube contains a hook for snaring the free end of the suture material; the inner tube contains a groove for retaining the suture loop circumferentially about the bore of the inner tube and also a hole beyond which the slip knot cannot move proximally. When the inner tube is pushed in a distal direction relative to the outer tube, the loop is pulled off the groove and is tightened. In use a grasping tool is inserted through the bore of the inner tube and is used to grasp a piece of tissue to be ligated. The device is then deployed, ligating the tissue piece.

18 Claims, 10 Drawing Sheets

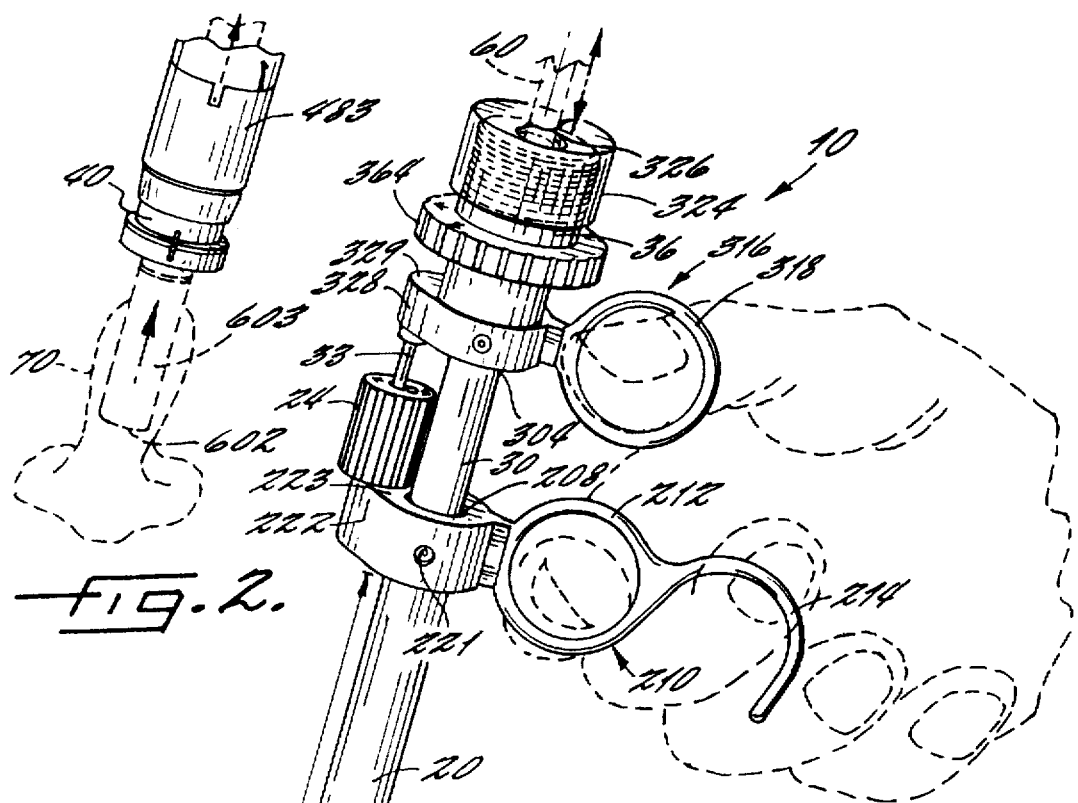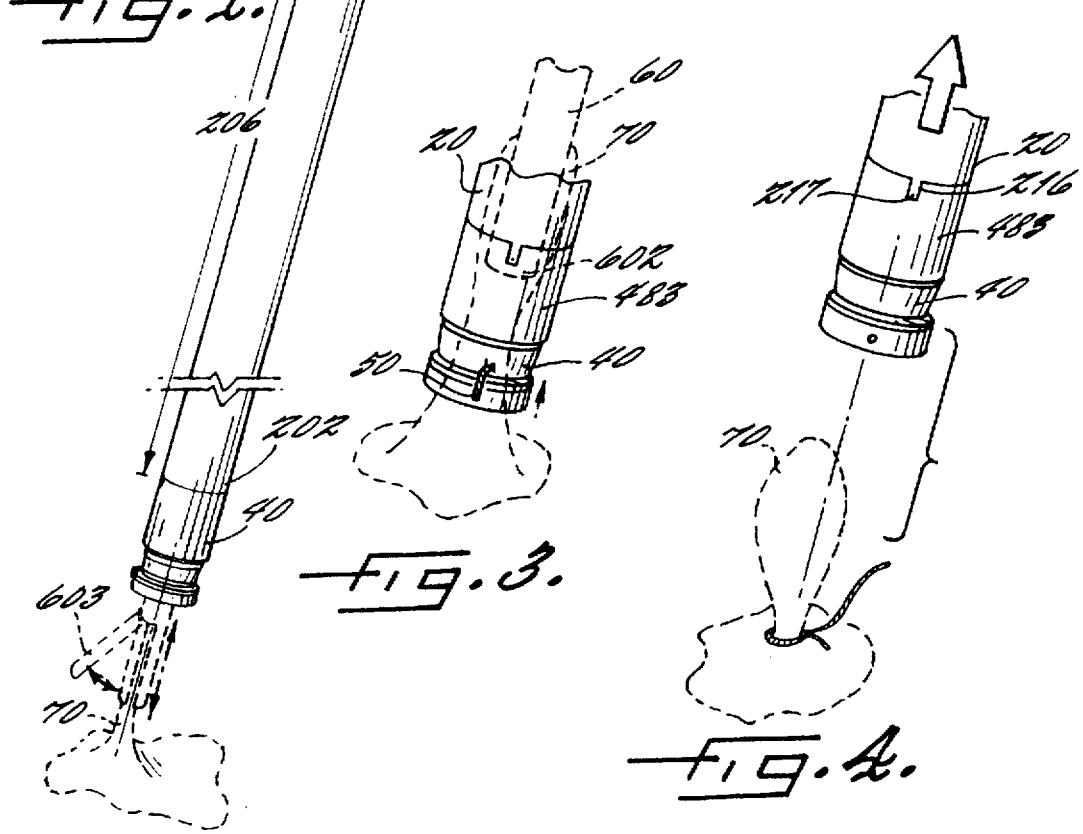

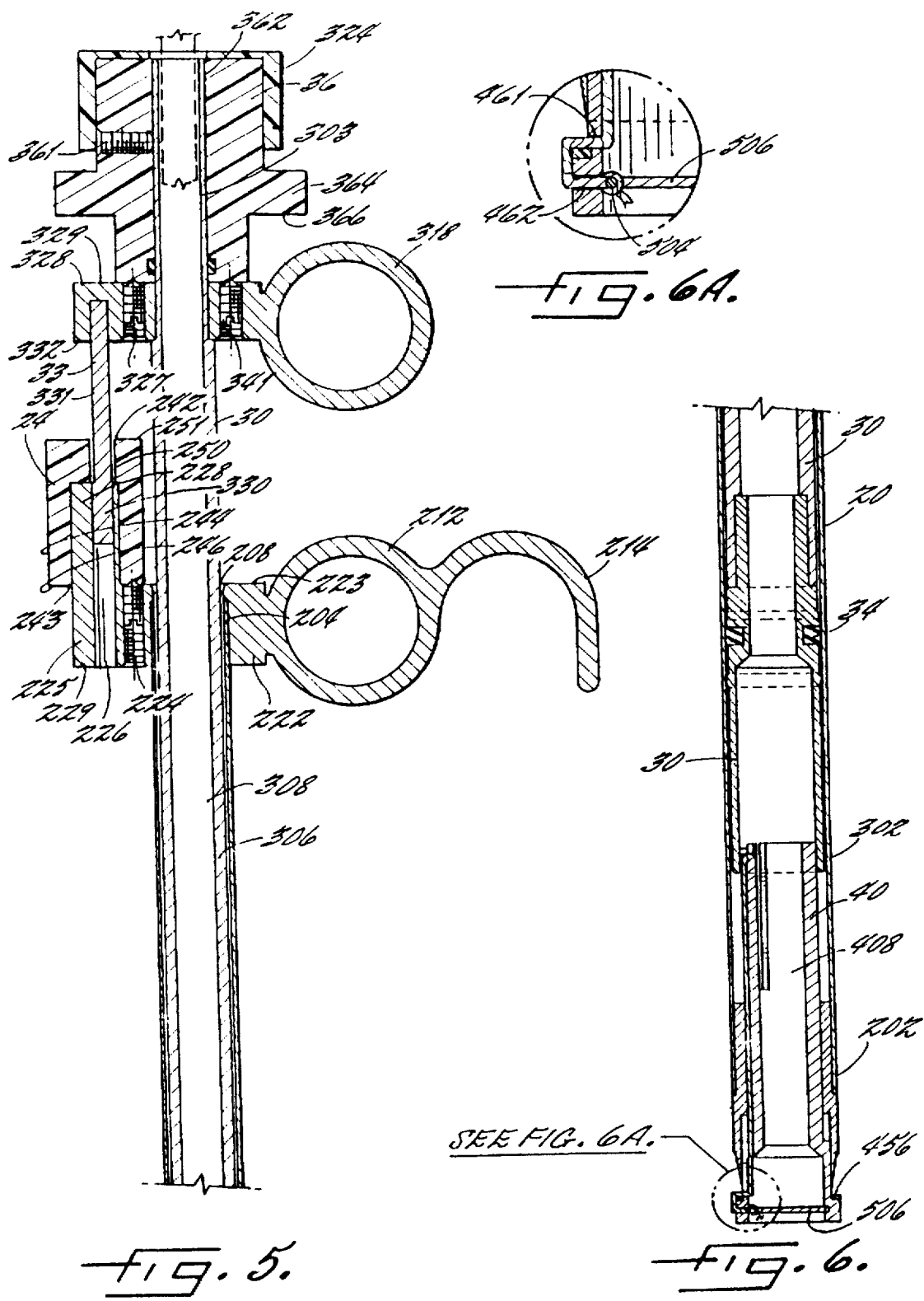

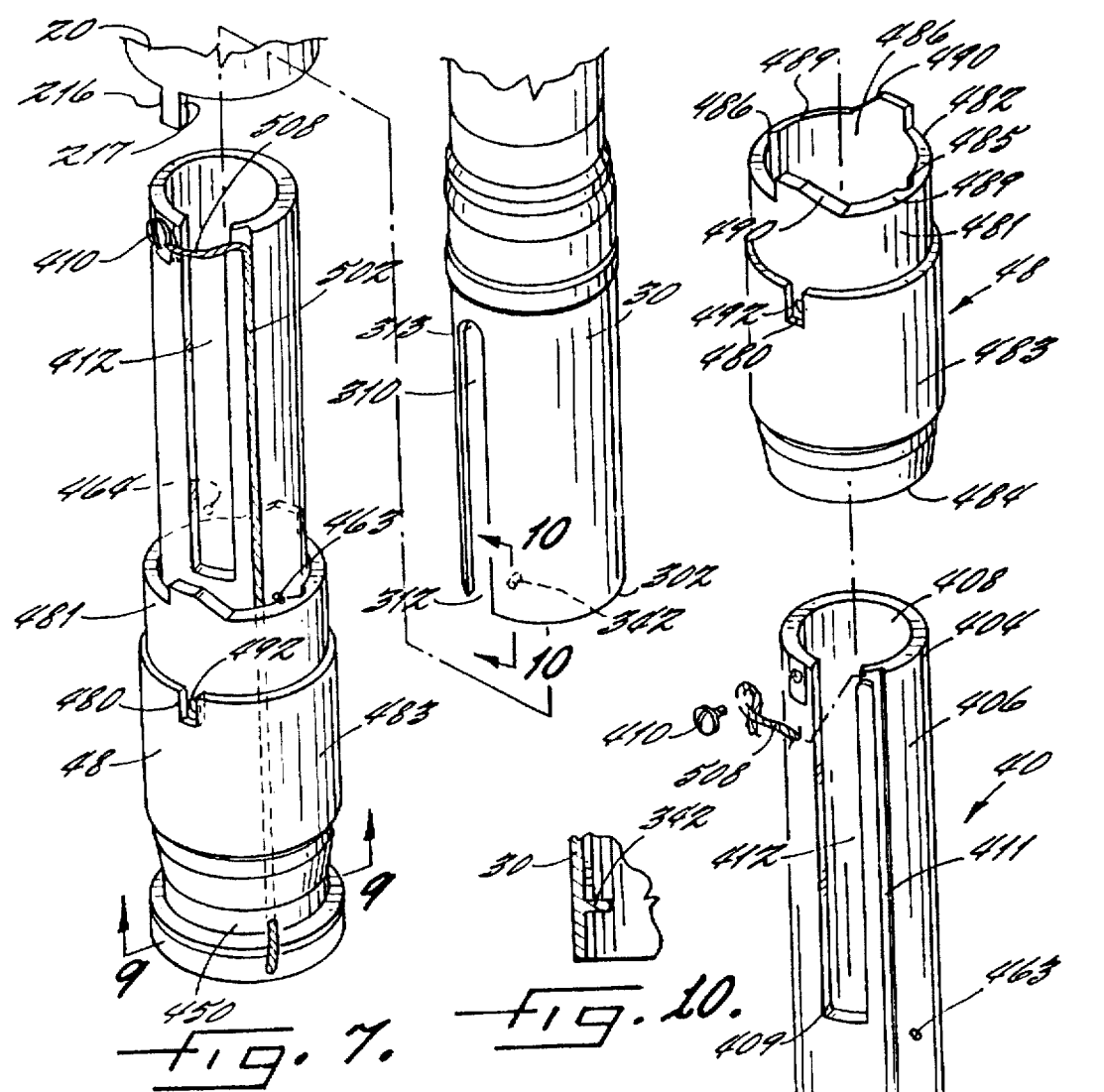
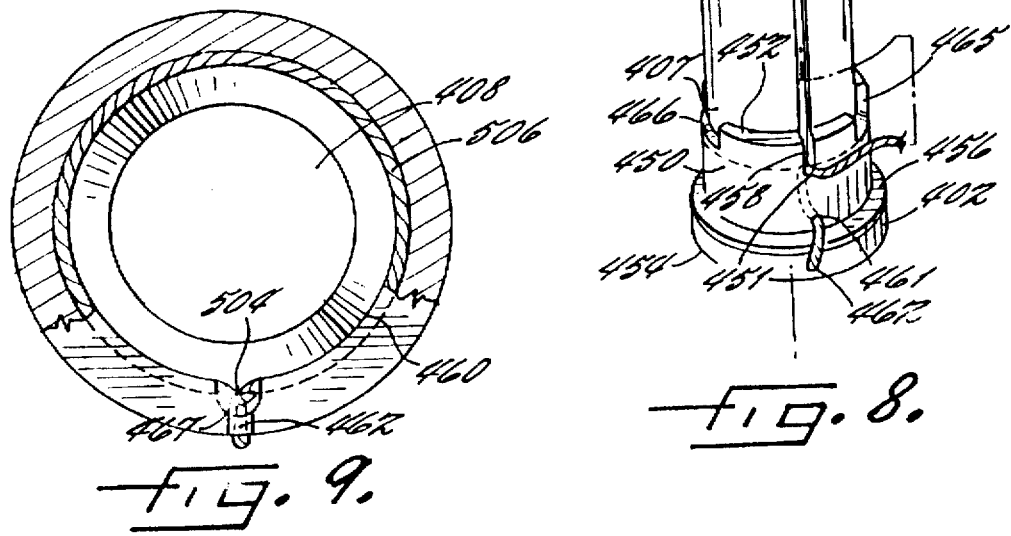

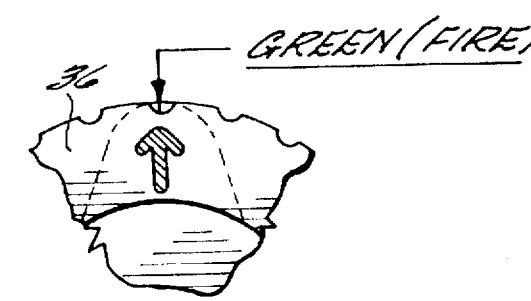
Fig. 17.
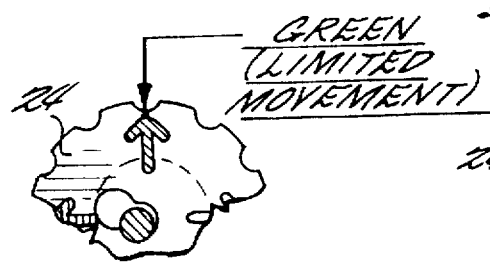
Fig. 18.
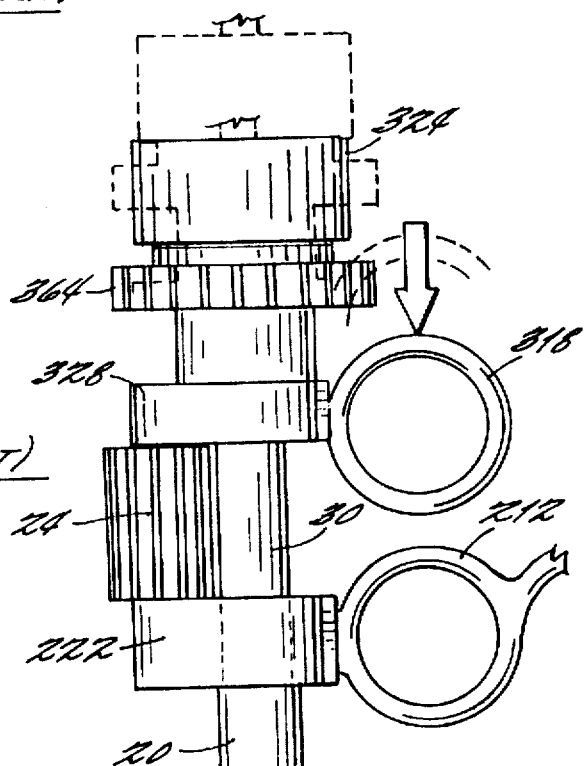
Fig. 19.
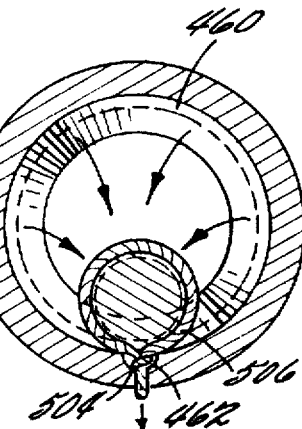
Fig. 21.
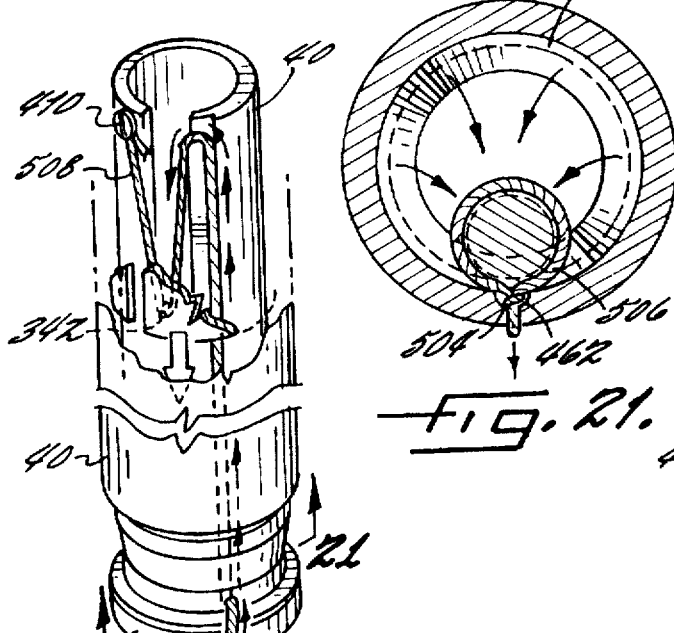
Fig. 20.
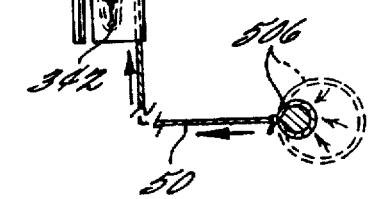

SURGICAL LOOP DELIVERY DEVICE AND METHOD

BACKGROUND OF THE INVENTION

1. Field of the Invention

The present invention relates to surgical devices and methods and, more particularly, to devices and methods for delivering a loop of suture material to a tissue segment for the purpose of ligation.

2. Description of Related Art

Modern surgical techniques often entail the use of endosurgery, wherein large incisions are avoided, and, instead, elongated instruments are inserted into and manipulated through trocars. Typically the surgical site, such as the peritoneum, is viewed remotely, and the surgeon works while watching a monitor.

Endoscopic applications of preknotted suture loops include the ligation of protruding pieces of tissue such as polyps or ends of blood vessels. Several devices are known in the art that deliver such suture loops to a site generally remote from the surgeon's hand and are remotely manipulable.

The tonsillotome of Longino (U.S. Pat. No. 1,468,599) contains a shank having a lumen wherein a suture loop resides and from which the loop is manipulable around a piece of tissue. Previously disclosed devices include those of Neivert (U.S. Pat. No. 1,833,687), who discloses a surgical snare comprising a fixed and a movable member capable of relative movement for tightening the snare loop that has been housed in the bore of the movable member.

The ligating loop device of Buelna (U.S. Pat. No. 5,242,459) has a shaft with a suture loop at its distal end, the loop having a slip knot. In addition, the device has a cutting element for severing the loop once it has been tightened. As with the device of Neivert, relative movement between two cylindrical members causes a tightening of the knot.

Noda et al. (U.S. Pat. No. 5,320,629) also contains relatively slidable members, one of which carries a suture with a slip knot at the end.

The endoscopic loop applying instrument of Kinet et al. (U.S. Pat. No. 5,405,351) both delivers the loop and cuts the free end of suture material.

The ligating instrument of Yoon (U.S. Pat. No. 5,486,186) also delivers a loop of suture material, the material extending through the lumen of an elongated device for being operated upon to tighten the loop around a piece of tissue. A cutter is also disclosed that is positioned within the lumen and is externally operable.

A problem shared by the above devices, however, is the difficulty in positioning and manipulating the suture loop, which must be accomplished with the use of a second portal and grasping instrument. In addition, the loop itself can collapse once inserted and thus lose its "loop" character, also making it difficult to snare a piece of tissue.

SUMMARY OF THE INVENTION

It is therefore an object of the present invention to provide a device and method that delivers to a surgical site a tightenable loop of suture material that is supported in an open position until the target tissue is snared.

It is an additional object to provide such a device and method that permits the passage of a grasping instrument through a common access portal with the device.

It is another object to provide such a device and method that permits the positioning of the grasping instrument through the loop prior to tightening.

It is a further object to provide such a device and method that includes means for cutting the free end of suture material from the tightened loop.

It is yet another object to provide such a device that can employ a cartridge preloaded with a loop of suture material and is therefore reusable with the introduction of a replacement cartridge.

It is yet an additional object to provide such a device that is operable with one hand.

These and other objects are achieved by the present invention, a device and method for delivering a loop of suture material for endoscopic ligation. The suture material, which may be preloaded onto the device prior to use, has a free end away from the loop and a slip knot that permits the loop to be tightened when the free end is pulled.

The suture loop delivery device comprises an outer tube that has a length commensurate with its intended use; that is, it must be sufficiently long to extend into the surgical site, typically through a trocar. The outer tube also has a longitudinal bore that extends from the tube's distal end to its proximal end.

The device further comprises an impelling member that has a distal portion dimensioned to freely slide within the outer tube bore, permitting relative sliding motion between a loading position and a deployed position, which is distal of the loading position. The impelling member also has a longitudinal bore extending from the distal end to the proximal end.

The suture material is preloaded onto a loop support member, which has a proximal portion that is dimensioned to reside within the outer tube bore. In a first embodiment, the proximal portion in turn has a proximal section that is dimensioned to reside within the impelling member bore. The loop support member also has a longitudinal bore extending from the distal to the proximal end.

The suture material is loaded onto the loop support member in such a way that the loop and the slip knot are retained thereon circumferentially so as to encircle the loop support member bore. The slip knot is prevented from moving in a proximal direction, but the loop is releasable from its supported position on the loop support member when tension is applied to the free end, which is affixed to the loop support member.

In the first embodiment, means are also provided for making accessible to the loop support member exterior an exposed length of suture material between the free end and the slip knot. This suture material exposed length is positioned so as to be snarable by an element positioned within the impelling member's bore, after the loop support member has been mated with the outer tube generally adjacent the outer tube's distal end.

During a loading operation the impelling member's distal portion is positioned within the outer tube. The loop support member, having a loop of suture material retained thereon, is mated to the outer tube, and its proximal portion is positioned within the outer tube bore, with its proximal end generally adjacent the impelling member's distal end. The exposed length of suture material is aligned with the snaring element.

The device is deployed in the first embodiment by pushing the impelling member in a distal direction relative to the outer tube, which causes the snaring element to snare the exposed length of suture material. Continued motion in the distal direction pulls the suture material, which causes the loop to tighten.

The bores of the outer tube, impelling member, and loop support member are generally coaxial and are dimensioned to permit the passage of a grasping tool through the assembled device. This permits the grasping tool to be inserted therethrough, which then may be used to grasp a piece of tissue. The device is then deployed to ligate the grasped piece of tissue.

In a particular embodiment means are also provided for cutting the suture material between the free end and the knot. The cutter has a cutting edge and is movable between a first position in spaced relation to the suture material and a second exposed position in cutting relation to the suture material between the free end and the knot. In use the cutting means is employed following a deploying of the device to sever the suture material loop from the loop support member.

In a second embodiment of the loop delivery device, the loop support member has a proximal portion that is dimensioned to reside at least partially within the outer tube bore. Means are provided for mating the loop support member with the impelling member at a position generally adjacent the impelling member's distal end.

In this embodiment, the snaring means is located within the outer tube bore in such a position to be able to snare the exposed length of suture material when in the deployed position. The device is then deployed by placing the impelling member within the outer tube. Then the loop support member, having a loop of suture material retained thereon, is mated to the impelling member and is positioned within the outer tube bore. In this position, the exterior section of suture material is snared. The impelling member is deployed by pushing the impelling member in a distal direction relative to the outer tube, pulling the snared exterior section of suture material against the slip knot, which serves to tighten the loop.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 illustrates the assembled device in the closed position, with a grasper inserted through the bore and grasping a piece of tissue.

FIG. 2 illustrates the distal end of the device, the grasper having grasped a piece of tissue and in position to pull the tissue piece into the device.

FIG. 3 illustrates the distal end of the device, the grasper having pulled the tissue into the device bore.

FIG. 4 illustrates the distal end of the device being removed from the ligating site, the loop having been tightened about the tissue and the free end of suture material having been cut away from the loop.

FIG. 5 is a longitudinal cross-sectional view of the proximal end of the device.

FIG. 6 is a longitudinal cross-sectional view of the distal end of the device.

FIG. 6A illustrates a detail of FIG. 6, showing the position of the suture knot when mounted on the loop support member.

FIG. 7 illustrates the mating of the loop support member with the impelling member.

FIG. 8 illustrates the loop support member and the pathway and mounting of the suture material thereon.

FIG. 9 is a transverse cross-sectional view adjacent the distal end of the loop support member, illustrating the positioning of the loop on the circumferential groove.

FIG. 10 is a detail from FIG. 7, illustrating the pin for snaring the suture material.

FIG. 13 is a detail of the actuator member in position for loading.

FIG. 14 is a detail of the locking member in the locking position.

FIG. 17 is a detail of the actuator member in position for firing.

FIG. 18 is a detail of the locking member in position to permit limited movement sufficient for firing.

FIG. 19 illustrates the device having been fired, the suture material snared by the pin, and the loop tightened.

FIG. 20 is a detail of the loop support member and impelling member, with the suture material having been snared.

FIG. 21 is a transverse cross-sectional view adjacent the distal end of the loop support member, the loop having been tightened and pulled away from the circumferential groove.

DETAILED DESCRIPTION OF THE PREFERRED EMBODIMENTS

Figure 11:
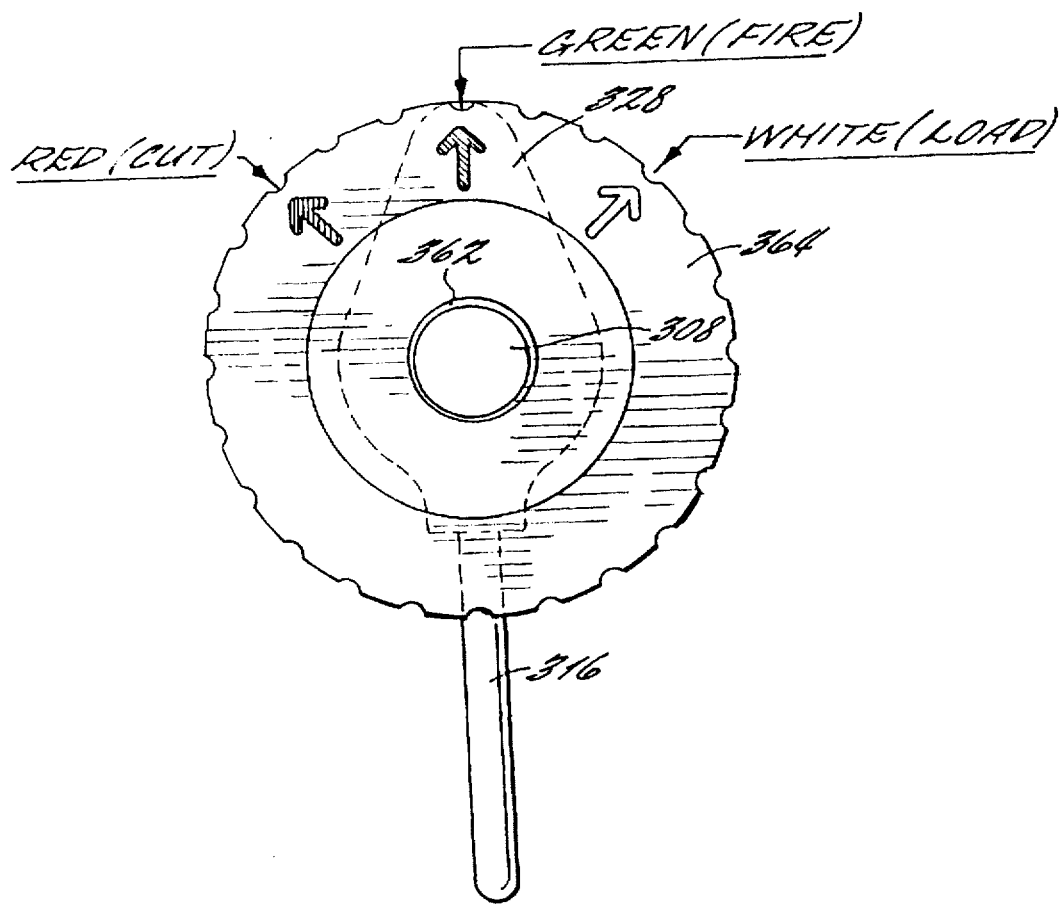
FIG. 11 is a top plan view of the actuator member.
Figure 12:
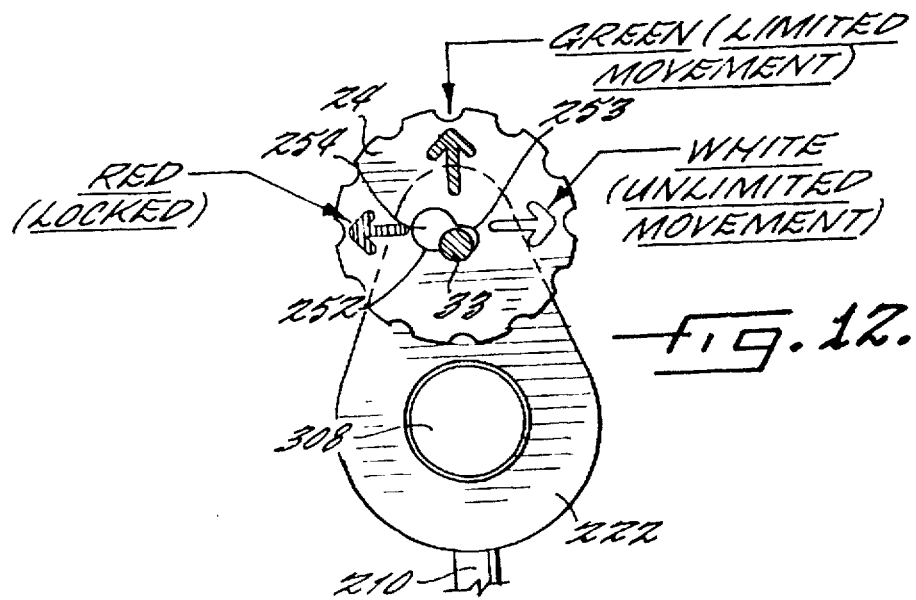
FIG. 12 is a top plan view of the locking member atop the first toroidal member, with the locking member in position to permit limited movement.
Figure 23:
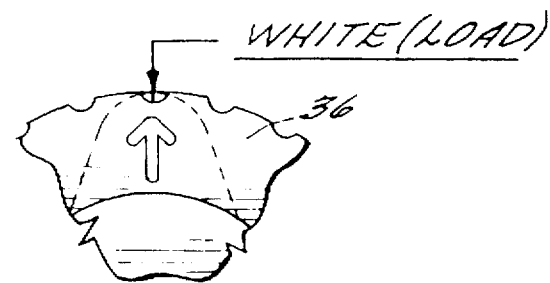
FIG. 23 illustrates the operation of the cutting assembly with the loop support member to cut the suture material.
Figure 24:
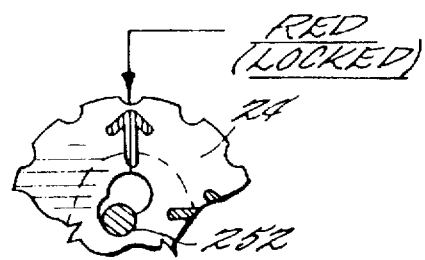
FIG. 24 is a detail of the cooperation between the cutting assembly ramp and the pin on the loop support member to effect a movement in the distal direction of the cutting assembly.
Figure 16:
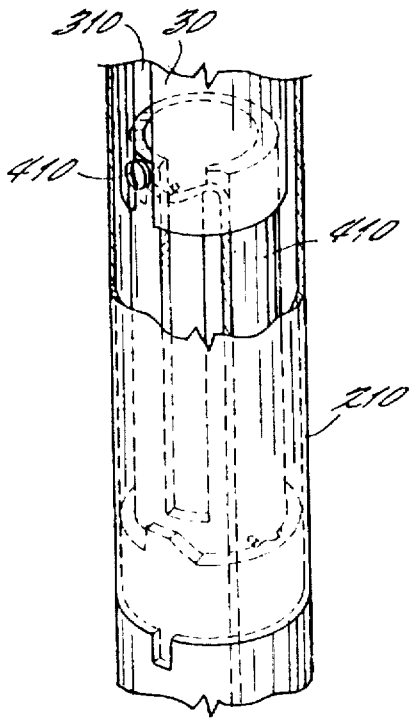
FIG. 16 illustrates the mated loop support member, impelling member, and outer tube, with the suture material snared by the pin.

A description of the preferred embodiments of the present invention will now be presented with reference to FIGS. 1–30.

Embodiment One

A first preferred embodiment 10 of the device to be described herein, shown assembled in FIGS. 1, 5, and 6, is for delivering a loop of suture material for endoscopic ligation. The suture material 50, which preparatory to the device's use is loaded onto the device 10, has a free proximal end 502 and a slip knot 504 for forming the loop 506 at the distal end and for permitting the loop 506 to be tightened (see FIG. 5).

The device 10 comprises an outer tube 20. Outer tube 20 has a length 206 and a longitudinal bore 208 that extends from the distal end 202 to the proximal end 204.

Figure 15:
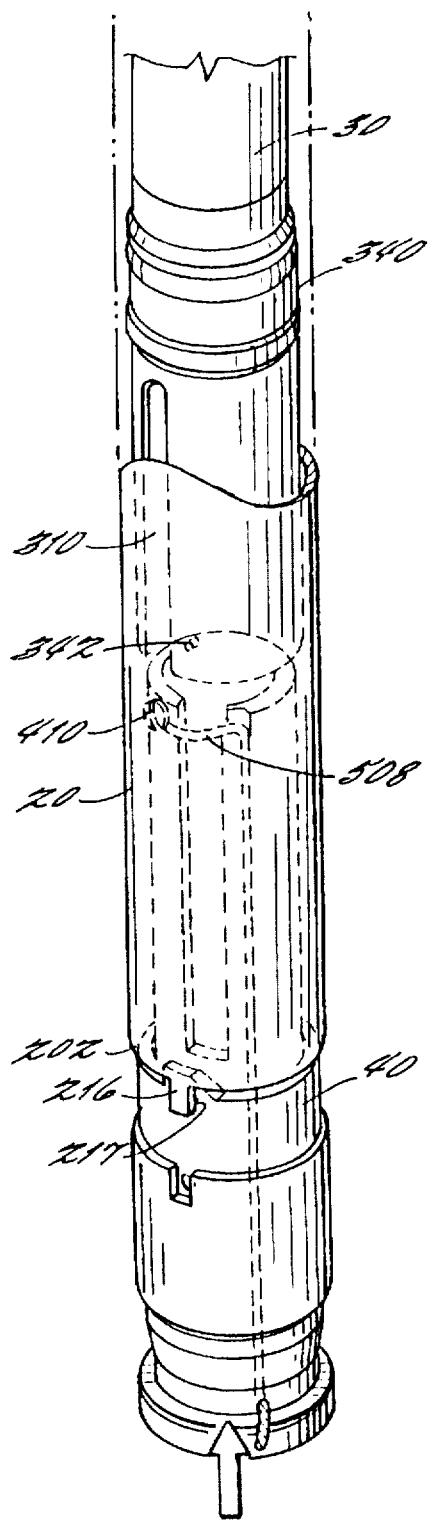
FIG. 15 illustrates the device distal end and the mating of the loop support member, the impelling member, and the outer tube.
Figure 22:
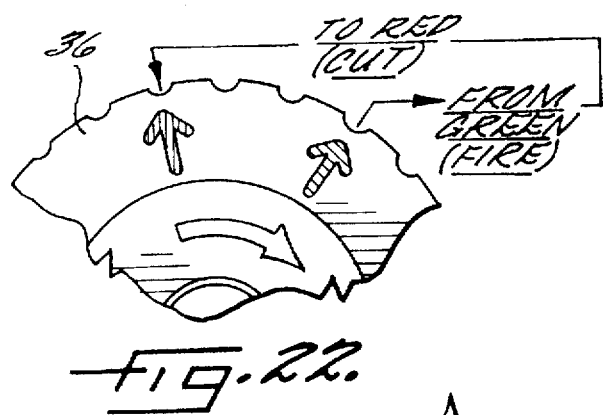
FIG. 22 is a detail of the actuator member in position for cutting.
Figure 24:
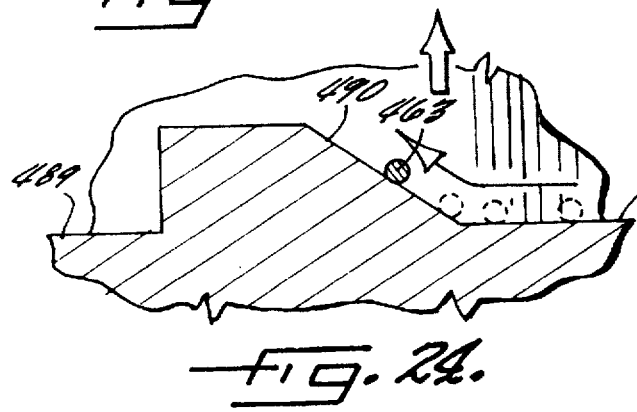
Figure 23:
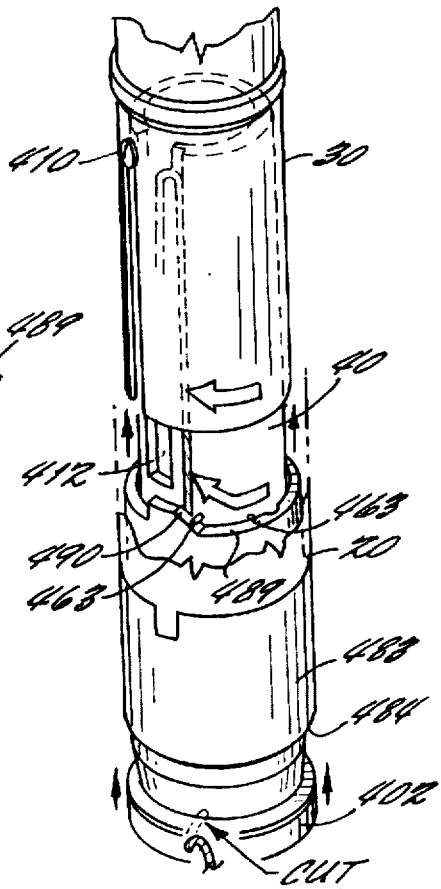
Figure 25:
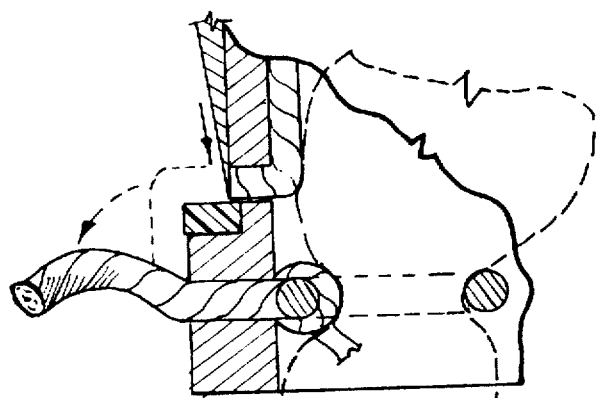
FIG. 25 is a longitudinal cross-sectional view of the cutting action of the cutting assembly blade upon the suture material to sever the loop, knot, and tissue from the device.

Extending distalward from the outer tube distal end 202 is a mating tab 216, having an inwardly facing tab protrusion 217 (see FIG. 15). Tab 216 is somewhat flexible, but is biased to a position wherein the outer surfaces of tab 216 and the outer tube distal end 202 are generally axially collinear. The purpose of the tab 216 will be discussed in the following.

A first grasping member 210 is affixed adjacent the outer tube's proximal end 204, which in the embodiment shown comprises a handle having a generally circular portion 212 and a downwardly curving portion 214 extending laterally therefrom. The circular portion 212 is dimensioned to permit the insertion of a finger, generally a middle finger or forefinger, of the surgeon; the curving portion 214 is dimensioned to permit the bracing of a finger, generally a third or middle finger, of the surgeon.

The circular portion 212 is affixed to the outer tube 20 by means of a first generally toroidal member 222 that encircles the outer tube 20 and is affixed via first set screw 221 to the exterior thereof. Generally laterally opposite the circular portion 212, and partially protruding above a proximal face 223 of the first toroidal member 222, is a ball and spring plunger mechanism 224, the spring portion and a distal section of the ball of which are housed within the first toroidal member 222.

Laterally adjacent and outside the plunger mechanism 224 is a proximally extending post 225. A longitudinal bore 226 extends completely through the post 225 and the first toroidal member 222. The bore 226 is noncentrally located relative to the post 225. An "L"-shaped groove (not shown) runs generally parallel to the bore 226 from the post's proximal end 228 to adjacent its distal end 229, makes a generally right-angle turn, and runs circumferentially adjacent the toroidal member 222 around the post 225 approximately 180 degrees.

A generally cylindrical locking member 24 has a bore 242, the distal section 243 of which is dimensioned to admit and slidably engage the post 225. Generally adjacent the locking member's distal end 244 and within the bore 242 is affixed an alignment pin (not shown), which is dimensioned to ride within the post groove. Disposed about the locking member's distal surface 246, generally at 90 and 180 degrees therefrom, are two radial grooves. The interaction between these grooves and the ball and spring plunger 224 provides two stable positions assumable by the locking member 24 relative to the post 225.

The proximal section 250 of the locking member bore 242 is dimensioned and positioned to permit locking, limiting, and assembling of the impelling member 30, which will be discussed in the following. From the proximal surface 251 this bore section 250 appears as a trilobed opening (see FIG. 12), with the lobes 252,253,254 of three different sizes, increasing in that order, used for, respectively, locking and limiting the impelling member 30 and assembling the device 10. Bore section 250 is narrower than the bore's distal section 243.

Device 10 further comprises an impelling member 30 (see FIGS. 1, 5, and 6) that has a distal portion 306 dimensioned to freely slide within the outer tube bore 208 and a longitudinal bore 308 that extends from the distal end 302 to the proximal end 304. Bore 308 is dimensioned to permit the passage of a grasping tool 60 therethrough, the function of which will be described in the following.

The impelling member 30 has a proximal section 301 having a first diameter. The distal portion 306 has a second diameter larger than the first diameter.

In general the impelling member distal portion 306 is slidable within and relative to the outer tube bore 208 between a first position (FIGS. 1 and 16) wherein the impelling member distal end 302 resides a first distance from the outer tube distal end 202 and a more distal position (FIGS. 19 and 20) wherein the impelling member distal end 302 resides a second distance to the outer tube distal end 202, the second distance less than the first distance. This will be shown in the following to achieve a tightening of the slip knot 504 to effect loop 506 tightening.

Toward the impelling member's distal end 302 is positioned an outer circumferential groove 340 dimensioned to seat an O ring 34 therein, for sealing the space between the outer tube 20 and the impelling member 30.

A second grasping member 316 is affixed adjacent the impelling member's proximal end 304, which in the embodiment shown in FIG. 1 comprises a handle having a generally circular portion 318 dimensioned to permit the insertion of a finger, generally a thumb, of the surgeon. When used in concert, the first 210 and the second 316 grasping members permit the surgeon to push the impelling member 30 distalward relative to the outer tube 20 in order to deploy the device 10, the details of which will be discussed in the following.

The circular portion 318 is rotatably affixed to the impelling member 30 by means of a second generally toroidal member 328 that encircles the impelling member 30 and is rotatable around the exterior thereof. The second toroidal member's bore 341 is dimensioned to closely engage the impelling member's proximal section 303 but to be smaller than the distal portion 306, which prevents it from moving distally.

Generally laterally opposite the circular portion 318, and protruding above a proximal face 329 of the second toroidal member 328, is a second ball and spring plunger mechanism 327, the spring portion and a distal section of the ball of which are housed within the second toroidal member 328. The purpose of this mechanism 327 will be discussed in the following.

Radially outward of the second ball and spring plunger mechanism 327 and protruding downward from the distal face 332 of the second toroidal member 328, generally parallel to the impelling member's longitudinal axis, is alignment and restraining rod 33, which has a proximal portion 331 and a larger-diameter distal portion 330. Rod 33 and locking member 24 operate in concert to permit the assembly, locking, and deploying of the device 10 as follows:

For assembly, locking member 24 is positioned so that, when the impelling member distal portion 306 is inserted into the outer tube bore 208, rod 33 is insertable into largest lobe 254, which is dimensonioned to permit the rod's distal portion 330 to pass therethrough, the second toroidal member's distal face 332 abutting the locking member's proximal surface 251.

Limiting the travel of the outer tube 20 and impelling member 30 relative to each other is achieved by turning the locking member 24 clockwise (as viewed from above) 90 degrees, so that the first radial groove and the first plunger mechanism 224 are opposed. This causes the rod's proximal portion 331 to be moved into the medium lobe 253, which is large enough to permit the rod's proximal portion 331 to travel freely therethrough, but which is too small to permit the rod's distal portion 330 to pass, thereby restraining the rod's distal portion 330 within the locking member bore 242.

Locking the relative movement of the outer tube 20 and the impelling member 30 is effected by turning the locking member 24 clockwise another 90 degrees, so that the second radial groove and the first plunger mechanism 224 are opposed. This causes the rod's proximal portion 331 to be moved into the smallest lobe 252, which is small enough to block any movement of the rod 33.

Within the impelling member's bore 308, in spaced relation to the distal end 302, is protrudes pin 342 for snaring the exposed length of suture material 508 (see FIG. 15). Adjacent the pin 342 in a clockwise direction is a generally longitudinal alignment slot 310 for mating with loop support member 40, which will be described in the following.

Atop the impelling member's proximal end 304 is placed a generally cylindrical actuator member 36 (see FIG. 11), which is affixed via second set screw 361 (FIG. 5) so that actuator member bore 362 surrounds the proximal section 303. Actuator member 36 comprises a serrated annular grasping portion 364 that protrudes radially outward to facilitate rotation. It can be seen that turning grasping portion 364 effects a rotation of the impelling member 30 relative to the second toroidal member 328.

Disposed about the actuator member's distal surface 366, generally at 45 and 90 degrees therefrom, are three radial grooves (not shown). The interaction between these grooves and the second ball and spring plunger 327 provides three stable positions (loading, deploying, and cutting) assumable by the actuator member 36 relative to the second toroidal member 328.

Atop the actuator member 36 is a protective cap 324, which is generally formed of a plastic material and has a deformable slit 326 dimensioned to be expandable for admitting a surgical implement such as a grasping tool 60 thereinto. Cap 324 serves to shield the proximal end 304 of the impelling member 30 and to prevent gas leakage from the surgical site.

The device 10 further comprises a generally cylindrical loop support member 40 that has a proximal portion 406 dimensioned to reside at least partially within the impeller member bore 308 (see FIGS. 6–10). The loop support member 40 also has a longitudinal bore 408 extending from the distal end 402 to the proximal end 404 that communicates with the impelling member bore 308 when those two elements are mated together. In a preferred embodiment the loop support member 40 has an outwardly projecting protrusion 410 adjacent the proximal end 404 that is dimensioned to slide within the slot 310 in the impelling member's distal portion 306. Mating is thus accomplished by lining up the protrusion 410 with the slot's 310 distal end 312, pushing the two elements together until the proximal end 313 of the slot 310 is reached. In this position, approximately half of the loop support member 40 resides within the impelling member bore 308 and is rotationally coupled thereto by the protrusion/slot 410/310 mating.

The loop support member proximal portion 406 further has a longitudinal slot 412 that extends from the proximal end 404 and has a length approximately the same as the impelling member slot 310. This slot 412, which communicates with bore 408, is positioned radially adjacent to and counterclockwise of protrusion 410, and is further positioned so that pin 342 rides therein when protrusion 410 is inserted into the impelling member bore 308 and rides along slot 310.

Radially adjacent to and counterclockwise of slot 412 is external groove 411, which extends from the proximal end 404 to the distal end 407 of proximal portion 406. Groove 411 does not communicate with bore 408.

Radially adjacent and counterclockwise of groove 411, and distal of the distal end 409 of slot 412 is first alignment pin 463, which protrudes radially outward. Second alignment pin 464, which also protrudes radially outward, is positioned approximately 180 degrees from the first alignment pin 463 and is clockwise of slot 412. These elements will be discussed in the following with regard to the cutting feature.

Affixed to the distalmost section of the proximal portion 406 is distal portion 450, a generally cylindrical member having a larger external diameter and a larger bore diameter than those of the proximal portion 406. The distal portion's proximal end 452 encompasses the proximal portion's distal end 407. At the distal portion's distal end 454 the distal portion 450 is widened further, creating a shoulder 456. The larger bore diameter at the distal end 454 is sufficient to permit the jaws of a grasping tool 60 to be opened at least partially therewithin.

A small slot 458 that communicates with bore 408 extends from the distal portion's proximal end 452 and is aligned with groove 411. Slot 458 is longer than the overlap between the proximal portion 406 and the distal portion 450, which leaves a window 451 through to the bore 408 that is sufficiently large to permit suture material 50 to pass therethrough.

Approximately 90 degrees radially from the slot 458 and 180 degrees from each other are two generally rectangular cutouts 465,466 in the distal portion's distal end 454 having a longitudinal extent less than the overlap between the proximal portion 406 and the distal portion 450. These elements will be discussed in the following with regard to the cutting feature.

Adjacent the distal portion's distal end 454 is a recessed circumferential groove 460 (FIG. 9) dimensioned to permit suture material 50 to fit thereinto and be held there when under no tension. Two radial holes 461,462 extend from the exterior of the distal portion 450 through to the bore 408. First hole 461 is distal of and generally axially aligned with slot 458. Second hole 462 is further distal yet, is generally axially aligned with slot 458, and communicates with circumferential groove 460, which at this point has an enlarged distal portion 467 that is sufficiently large to retain the suture material's slip knot 504 therein. Proximal of its distal portion 467, however, second hole 462 is too small to permit the slip knot 504 to pass therethrough. This dimensioning thereby serves to restrain the slip knot 504 from proceeding in a proximal direction beyond the enlarged distal portion 467.

The suture material 50 is thus loaded onto and supported on the loop support member 40 as follows (see FIGS. 6A, 8 and 9): The suture loop 506 is positioned within the inner groove 460, with the slip knot 504 positioned within the second hole's enlarged distal portion 467 adjacent the second hole 462. Thus the loop 506 when loaded encircles the loop support member bore 408.

The suture material's free end 502 is threaded from within the bore 408 to the exterior surface via second hole 462 and then back into the bore 408 via first hole 461. The free end 502 is next threaded from the bore 408 to the exterior surface via window 451 and is positioned within slot 458 and groove 411.

At the proximal portion's proximal end 404 the suture material 50 crosses the slot 412 in a clockwise direction and is affixed to the proximal end 404, leaving an exposed length 508 of suture material 50 across the slot 412. In the embodiment shown, the suture material 50 is affixed with protrusion 410, shown here as a screw; however, it may be appreciated that the affixing may be accomplished by any means known in the art, such as heat staking.

When tension is applied to the free end 502 by snaring and pulling on the exposed length 508, as shown in FIGS. 19–21, tension is transmitted to the loop 506, and the slip knot's 504 being retained at the second hole 462 causes the loop 506 to tighten. The inner groove 460 is shaped with no or minimal inner shoulder, thereby permitting the loop 506 and slip knot 504 to slide off the groove 460 during tightening.

The snaring and pulling of the exposed length 508 of suture material 50 for tightening are accomplished as follows: The loop support member 40 is mated to the impelling member 30 as described previously, the pin 342 positioned to snare the suture material exposed length 508, which sets the device 10 for deploying. The device 10 is then deployed by pushing the first 210 and the second 318 grasping members toward each other until the first 222 and the second 328 toroidal members sandwich the locking member 24 between them. This pushes the impelling member 30 in a distal direction relative to the outer tube 20 and to the loop support member 40, and the pin 342 pulls the snared exposed length 508 of suture material 50 in a distal direction, thereby tightening the loop 506.

In a preferred embodiment of the invention, means are provided for cutting the suture material 50 between the slip knot 504 and the free end 502. In general, the cutter has a cutting edge that is movable between a first position in spaced relation to the suture material 50 and a second position in cutting relation to the suture material 50 between the slip knot 504 and the free end 502.

Specifically, this is accomplished in a particular embodiment, illustrated in FIGS. 7, 8, and 23–25, with a generally cylindrical cutting assembly 48. Cutting assembly 48 has a proximal portion 481 having a proximal end 482, a wider distal portion 483 having a sharpened distal end 484, and a longitudinal bore 486. A shoulder 493 separates the distal portion 483 from the proximal portion 481 and encircles the cutting assembly 48. A cutout 480 in the distal portion 481 extends distalward from the shoulder 493, the depth of which matches the width of the shoulder 493. Within the cutout 480 is an inwardly extending dimple 492. The cutout 480 and dimple 492 are dimensioned to be matable with the tab 216 and protrusion 217, respectively.

The cutting assembly's bore 486 is sufficiently large to permit the cutting assembly 48 to surround the loop support member's proximal portion 406 and distal portion proximal end 452, but too small to pass beyond the shoulder 456 leading to the loop support member's distal portion's distal end 454. Bore 486 is also too small to permit the cutting assembly 48 to pass beyond the protrusion 410. Therefore, protrusion 410 and shoulder 456 serve to retain cutting assembly 48 in surrounding relation to the loop support member 40. These parts are thus assembled by sliding the cutting assembly 48 over the loop support member's proximal end 404 prior to affixing protrusion 410 thereto.

The cutting assembly's proximal portion 481 is sufficiently small to permit entry into the outer tube's bore 208; the distal portion 483 is too large to fit thereinto. Mating the cartridge, which comprises the loop support member 40 and the cutting assembly 48, with the outer tube 20 is achieved by inserting the loop support member's proximal end 452 and cutting assembly's proximal portion 481 into the outer tube bore 208, with the tab 216 aligned with cutout 480. When the tab 216 is pushed sufficiently far into cutout 480 that protrusion 217 snaps into dimple 492, a kinetic coupling between the cutting assembly 48 and the outer tube 20 is achieved (see FIG. 15).

The cutting assembly's proximal end 482 is contoured (see FIG. 8). Two generally flat portions 489 are generally 180 degrees apart. Two proximally extending ramps 490, meeting the flat portions 489 radially, are also generally 180 degrees apart. The ramps 490 each slope upward (in a proximal direction) proceeding clockwise (viewing in a distal direction) and end in a downward (distally extending) shoulder that meets the opposite flat portion 489.

When in the assembled position, with the cutting assembly 48 in surrounding relation to the proximal end 452 of the loop support member's distal portion 450, alignment pins 463,464 further restrict the longitudinal movement of the cutting assembly 48, as the pins' 463,464 radial extent is larger than the diameter of bore 486 (see FIG. 7). Two interior longitudinal grooves 485,486 extend from the cutting assembly's proximal portion's proximal end 482 to the distal portion's distal end 484 and are radially positioned along the flat portions 490 of the proximal end 482. Grooves 485,486 are spaced approximately 180 degrees from each other and are dimensioned to permit alignment pins 463,464 to travel therein. Bore 486 and grooves 485,486 are therefore dimensioned and positioned to permit a proximal movement of the cutting assembly 48 relative to the loop support member 40 when the pins 463,464 are positioned within the grooves 485,486.

Pins 463,464 are further positioned so that, when the pins 463,464 are proximal of the cutting assembly's proximal end 482, and when the cutting assembly 48 is rotated relative to the loop support member 40 in a counterclockwise direction, pins 463,464 ride along the cutting assembly's proximal end 482. Thus, if pins 463,464 are proximal of grooves 485,486, a counterclockwise rotation will cause the cutting assembly 48 to move in a distal direction as the pins 463,464 engage the ramps 490. The cutting assembly 48 and loop support member 40 are further dimensioned so that, when the pins 463,464 approach the top of the ramps 490, the cutting assembly's sharp distal end 484 abuts the loop support member's shoulder 456. In this position, since the suture material 50 when loaded passes over the shoulder 456 when proceeding from the first hole 461 to the second hole 462, the suture material 50 is cut.

Since the outer tube 20 and the cutting assembly 48 are coupled, and the impelling member 30 and the loop support member 40 are also coupled, a relative rotation of the outer tube 20 versus the impelling member 30 will transmit this relative rotation to the cutting assembly 48 and the loop support member 40.

Protruding into the cutting assembly's bore 486 are third and fourth alignment pins (not shown), which are radially spaced at approximately 180 degrees and are spaced from the distal end 484. The third and fourth pins are positioned and dimensioned so that, when the cutting assembly's distal end 484 is adjacent the loop support member's shoulder 456, the pins engage the cutouts 465,466 in the distal portion 450 and prevent relative rotation therebetween beyond the radial extent of the cutouts 465,466.

The device 10 is utilized to ligate a piece of tissue and cut the loop 506 from the device 10 as follows:

The device 10 is assembled and loaded (FIGS. 7, 8, and 13–16) by threading suture material 50 onto the loop support member 40 as described, placing the cutting assembly 48 over the loop support member 40, and affixing the suture material free end 502 and screw 410 adjacent the loop support member's proximal end 404.

The outer tube 20, with the first toroidal member 222, first grasping member 210, and locking member 24 affixed thereto, is mated to the loop support member 40 by inserting the tab 216 into the cutout 480 until the protrusion 217 snaps into the dimple 492.

The impelling member 30 is mated with the second toroidal member 328, second grasping member 316, rod 33, actuator 36, and cap 324 as described above. The impelling member's distal end 302 is inserted into the outer tube's bore 208, and the unit is aligned so that the rod 33 may be inserted into the locking member's bore 242. In order to load, the actuator 36 is turned to the loading position, painted white in an exemplary model, and the locking member 24 is turned to the "unlimited movement" position, also painted white in the exemplary model. When the impelling member 30 is in place, the locking member 24 is turned to the "locked" position, painted red in the exemplary model, to prevent accidental firing of the unit.

The device 10 is then inserted into the surgical site, typically through a trocar placed through an incision into a body cavity, although this use is not intended as limiting. A grasping tool 60 is inserted through the impelling member bore 308 and the loop support member bore 408 (FIG. 1) and is used to grasp a piece of tissue 70 to be ligated (FIG. 2) with its jaws 603. Next the grasping tool 60 is pulled in a proximal direction to pull the grasped tissue 70 into the loop support member bore 408 (FIG. 3) sufficiently far that the distal end 602 of the grasping member's jaws 603 are proximal of the suture loop 506.

The device 10 is then prepared for deploying (firing) to ligate the grasped piece of tissue 70 (FIGS. 17–21). This is accomplished by moving the actuator to the "fire" position, painted green in the exemplary model, and rotating the locking member 24 into the "limited movement" position, also painted green in the exemplary model. In these positions the impelling member 30 and outer tube 20 are free to move toward one another, but not to disengage fully.

The first 210 and the second 316 grasping members are grasped, and deploying is accomplished by pushing the second grasping member 316 distalward relative to the first grasping member 210, until they are as close together as possible. Their relative movement will be stopped when the locking member 24 is sandwiched between the first 222 and the second 328 toroidal members. As discussed previously, this movement permits the protrusion 342 on the outer surface of the impelling member 30 to snare the exposed length 508 of suture material and pull it downward, exerting tension on and tightening the suture loop 506, which is pulled off the groove 460 to surround and ligate the grasped tissue 70.

Next the cutting assembly 48 is engaged to cut the suture loop 506 away from the remaining suture material 50 (FIGS. 22–25). First the locking member 24 is moved back to the "locked" position to prevent relative movement between the impelling member 30 and the outer tube 20. Then, as the actuator 36 is rotated clockwise from the "firing" to the "cutting" position, the cutting assembly 483 is rotated relative to the loop support member 40 and is forced in a distal direction, which forces the sharp distal end 484 of the cutting assembly 48 against the loop support member's shoulder 456, cutting the suture material 50. This releases the loop 506 and ligated tissue 70.

Figure 26:
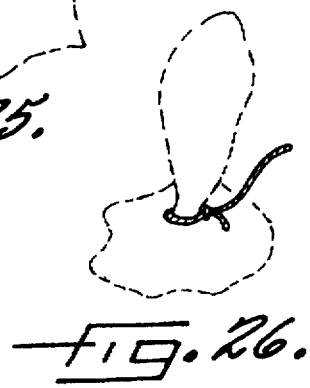
FIG. 26 illustrates the snared tissue with the loop and knot cut from the remaining suture material and separated from the device.
Figure 27:
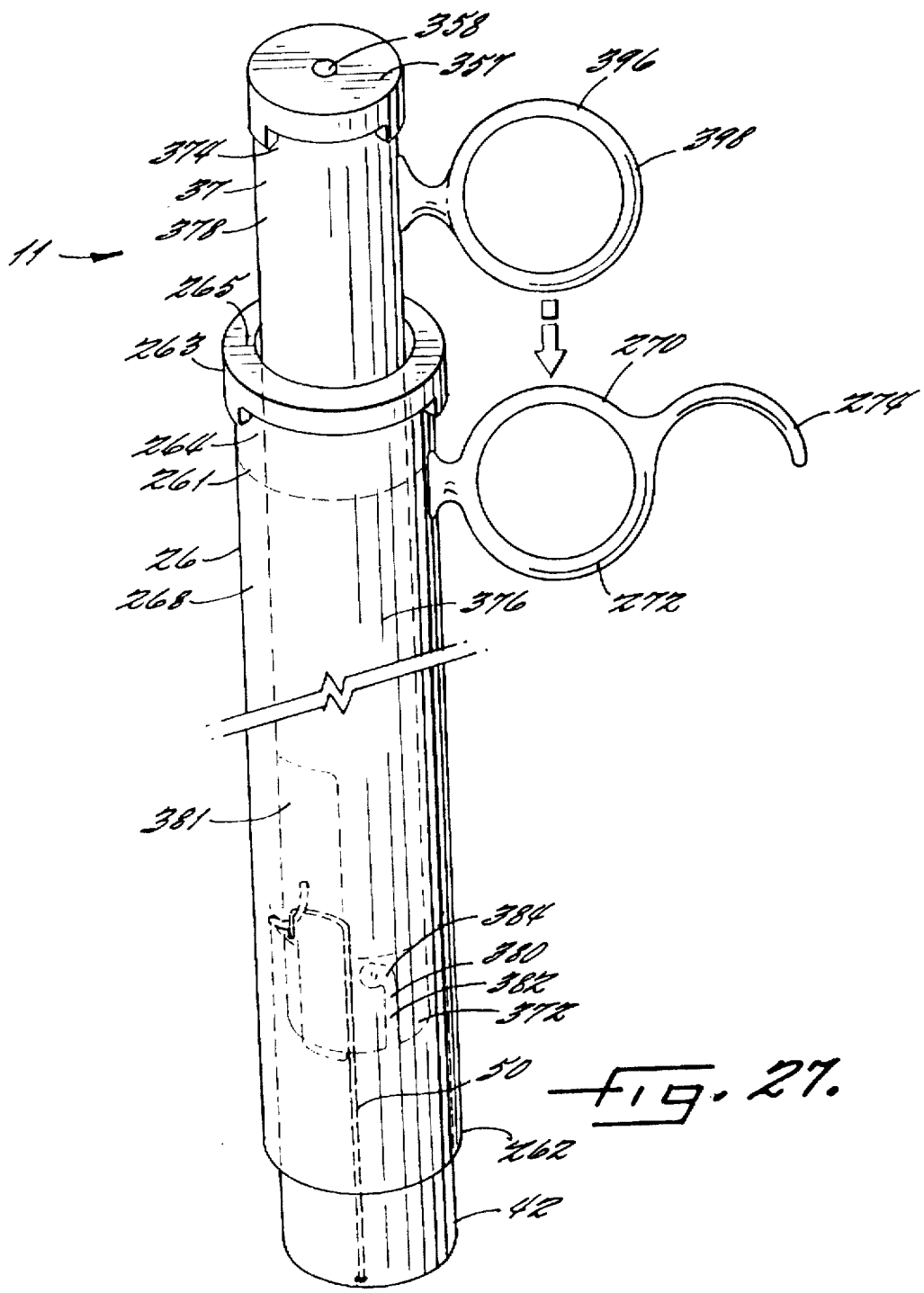
FIG. 27 is a perspective side view, partially cut away, of the second embodiment of the device, showing the distal end and the mating of the loop support member, the impelling member, and the outer tube.

Finally, the device 10 is removed from the site (FIG. 4) leaving the ligated tissue 70, loop 506, and knot 504 behind (FIG. 26). This tissue can then be left at the site as is, or removed by other means.

Embodiment Two

A second embodiment of the device 11 and method of the present invention (FIGS. 27–30) is also for delivering a loop of suture material for endoscopic ligation. The suture material 50, which preparatory to the device's use is loaded onto the device 11, has a free end 502 and a slip knot 504 therein for permitting the loop 506 to be tightened (see FIGS. 28 and 29). The device 11 comprises an outer tube 26, which has a length and a longitudinal bore 268 that extends from the distal end 262 to the proximal end 264. Within the bore 268 adjacent the proximal end 264 is affixed a gasket 261 for maintaining gas pressure and also for aligning the impelling member in the bore 268, which will be discussed in the following. Atop the proximal end 264 is placed first protective cap 263, which is generally formed of a plastic material and also has a bore 265. Cap 263 serves to shield the proximal end 264 of the outer tube 26, which, if the outer tube 26 is made of metal, could pose a risk to the surgeon.

A first grasping member 270 is affixed adjacent the proximal end 264, which in the embodiment shown comprises a handle having a generally circular portion 272 and a downwardly curving portion 274 extending therefrom. The circular portion 272 is dimensioned to permit the insertion of a finger, generally a middle finger, of the surgeon; the curving portion 274 is dimensioned to permit the bracing of a finger, generally a third finger, of the surgeon.

Device 11 further comprises an impelling member 37 that has a distal portion 376 dimensioned to freely slide within the outer tube bore 268, a distal end 372, a proximal end 374, and a longitudinal bore 378. Bore 378 extends from the distal end 372 to the proximal end 374 and is dimensioned to permit the passage of a grasping tool 60 therethrough, as described above for the first embodiment.

In general the impelling member 37 is slidable within and relative to the outer tube bore 268 between a first position (FIG. 27) wherein the impelling member distal end 372 resides within the outer tube bore 268 and a second, more distal, position (FIG. 30) wherein the impelling member distal end 372 is generally adjacent, or may protrude beyond, the outer tube distal end 262. This will facilitates a mating of a loop support member 42 to the impelling member 37 utilizing an "L"-shaped notch 380 in the distal end 372. The distalmost portion 382 of the notch 380 is generally parallel to the long axis of the outer tube 26. The cross-portion 384 of the notch 380 is generally perpendicular to the distalmost portion 382. Notch 380 in the embodiment shown communicates with the impelling member bore 378.

Adjacent the "L"-shaped notch 380 and extending from the distal end 372 is slot 381, which also communicates with the bore 378.

Atop the impelling member's proximal end 374 is placed second protective cap 357, which is generally formed of a plastic material and also has a bore 358. Cap 357 serves to shield the proximal end 374 of the impelling member 37, as discussed above with respect to the outer tube 26 for protecting the surgeon.

A second grasping member 396 is affixed adjacent the proximal end 374, which in the embodiment shown comprises a handle having a generally circular portion 398. The circular portion 398 is dimensioned to permit the insertion of a finger, generally a thumb, of the surgeon. When used in concert, the first 270 and the second 396 grasping members permit the surgeon to slide the impelling member 37 relative to the outer tube 26 in order to deploy the device 11, the details of which will be discussed in the following.

Figure 28:
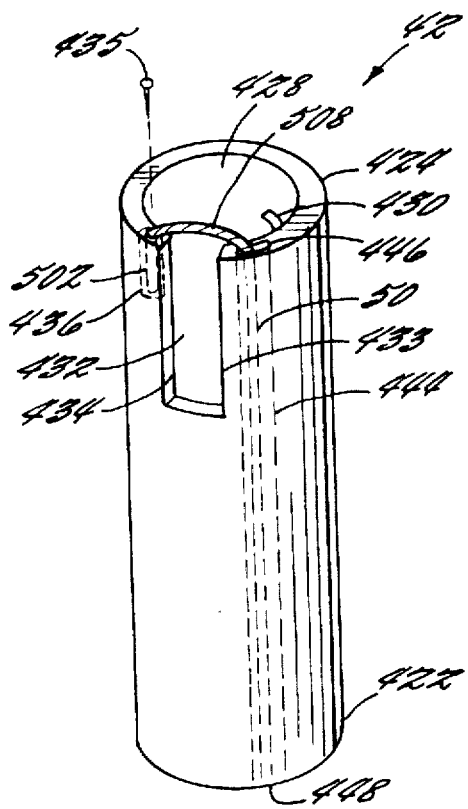
FIG. 28 illustrates the loop support member of the second embodiment and the pathway and mounting of the suture material thereon.
Figure 29:
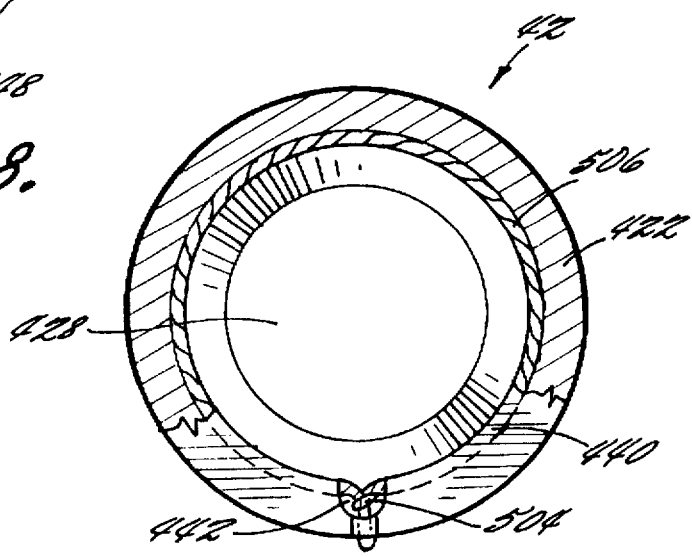
FIG. 29 is a distal end view of the loop support member of the second embodiment illustrating the disposition of the suture material thereon.

The device 11 further comprises a generally cylindrical loop support member 42 that has a proximal portion dimensioned to reside at least partially within the outer tube bore 268 (see FIGS. 28 and 29). The loop support member 42 also has a longitudinal bore 428 extending from the distal end 422 to the proximal end 424 that communicates with the impelling member bore 378 when those two elements are connected together. In a preferred embodiment the loop support member 42 has a protrusion 430 extending into the bore 428 and adjacent the proximal end 424 that is positioned and dimensioned to slide within the 'L'-shaped notch 380. Mating is accomplished by lining up the protrusion 430 with the notch distalmost portion 382, pushing the two elements together until the end of the distalmost portion 382 is reached, and twisting the loop support member 42 so that the protrusion 430 tracks along the notch cross-portion 384, thereby locking the elements together.

When the loop support member 42 is mated with the impelling member 37, impeller slot 381 is generally aligned with loop support member slot 432.

The suture material 50 is loaded onto and supported on the loop support member 42 as follows: Adjacent the distal end 422 and adjacent the loop support member bore 428 is an inner circumferential groove 440 adapted to retain the suture material loop 506 and slip knot 504 thereon when the loop 506 is not under tension. In the preferred embodiment, a wider section 442 of the groove 440 is provided for retaining the slip knot 504. Thus the loop 506 when loaded encircles the loop support member bore 428. When tension is applied to the free end 502, the groove 440 is shaped to permit the loop 506 and slip knot 504 to slide off the groove 440 for tightening.

In order to affix the free end 502 of suture material 50 to the loop support member 40, a second bore 444 generally parallel to the first bore 428 is provided that extends from the proximal end 424 to the distal end 422. This second bore 444, which is preferably located so as to have its distal end 448 emerge into the wider groove section 442, is dimensioned to permit suture material 50 to pass therethrough, but to block the passage of the slip knot 504. Thus, if tension is applied to the free end 502 of suture material 50 emerging from the proximal end 446 of the second bore 444, the slip knot 504 is retained adjacent the distal end 448 of the second bore 444, and the loop 506 is tightened. The second bore 444 is smaller than the first bore 428, which is dimensioned to permit a grasping tool 60 to pass therethrough.

The loop support member 42 further has a notch 432 that communicates with the first bore 428 and is positioned adjacent the proximal end 424. The notch 432 is also positioned so as to have the second bore 444 on a first side 433 of the notch 432.

The suture material free end 502 is affixed adjacent the second side 434 of the notch 432. In a particular embodiment a pin 435 pierces the free end 502 and is inserted into a third bore 436 in the loop support member 42 that is also generally parallel to the first bore 428. Therefore, when in use the suture material free end 502 emerging from the second bore proximal end 446 is affixed so as to cross the notch 432 from the notch first side 433 to the notch second side 434, which makes a section 508 of suture material 50 available to the exterior of the loop support member 40.

In order to snare the exterior section 508 of suture material 50, a hook 282 is affixed within the outer tube bore 268 in such an axial position that, when the impelling member 37 is pulled into the first position within the outer tube bore 268, the loop support member 42 having been mated to the impelling member 37, the hook 282 snares the suture material exterior section 508, which sets the device 11 for deploying. The hook 282 is also positioned to ride within the impeller slot 381. The device 11 is deployed by pushing the impelling member 37 in a distal direction relative to the outer tube 26, pulling the snared exterior section 508 of suture material 50 and thereby tightening the loop 506 (FIG. 30).

The device 11 is utilized with a grasping tool 60 as follows: The grasping tool 60 is inserted through the impelling member bore 378; the grasping tool 60 is used to grasp a piece of tissue 70 to be ligated; and the device 11 is deployed to ligate the grasped piece of tissue 70. This is analogous to the procedure discussed above for the first embodiment.

Figure 30:
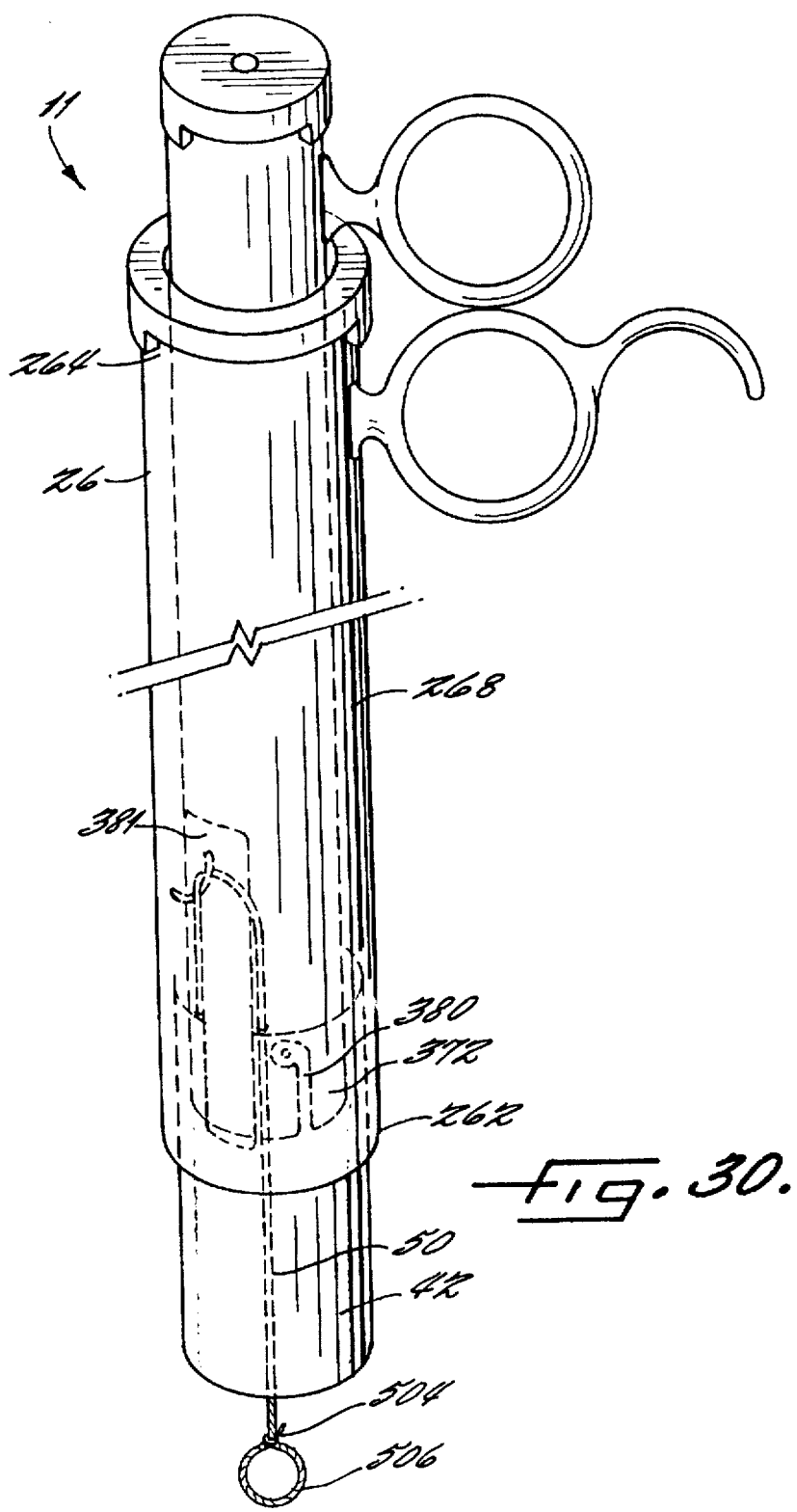
FIG. 30 illustrates the second embodiment of the device having been fired, the suture material snared by the hook, and the loop tightened.

Means for limiting the distalward sliding is accomplished by the abutment of the circular portions 272,398 of the first 270 and second 396 grasping members (see FIG. 30).

It may be appreciated by one skilled in the art that additional embodiments may be contemplated, including those having alternate means of retaining the loop of suture material in an opened configuration, as well as alternate means of affixing the suture material free end to the outer tube and means of snaring the exposed length of suture material.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for delivering a loop of suture material for endoscopic ligation, the suture material having a free end and a slip knot therein for tightening the loop, the device comprising:

a generally cylindrical loop support member having:
  a longitudinal bore extending from a loop support member distal end to a loop support member proximal end, the bore dimensioned to permit a grasping device to pass therethrough;
  means for releasably retaining the loop of suture material circumferentially thereon, the loop thereby encircling the longitudinal bore;

means for affixing the free end of suture material to the loop support member; and a loop-tightening aperture positioned between the loop retaining means and the affixing means and dimensioned sufficiently large to permit a passage of the suture material but insufficiently large to permit a passage of the slip knot, wherein in use tension applied to the free end causes a closing of the suture loop; and means for snaring a portion of suture material between the free end and the slip knot, the snaring means movable between a loading position wherein the suture material snared portion is generally free from tension and the loop is retained on the loop retaining means and a deployed position wherein the suture material snared portion is pulled by the snaring means, applying tension thereto, and thereby tightening the loop.

2. The suture loop delivery device recited in claim 1, wherein the loop support member has a distal face at the distal end and the loop retaining means comprises a groove in the distal face encircling the bore, the groove dimensioned to permit suture material to reside therein.

3. The suture loop delivery device recited in claim 2, wherein:

the affixing means is positioned adjacent the loop support member proximal; and the loop support member further comprises means for guiding suture material between the aperture and the affixing means.

4. The suture loop delivery device recited in claim 3, wherein:

the loop support member further has a slot extending distalward from the proximal end and communicating with the bore, the slot positioned circumferentially between the affixing means and a proximal end of the guiding means, the suture material when positioned on the loop support member passing across the slot, exposing a length of suture material; and the snaring means comprises:

a generally cylindrical member dimensioned to surround at least a proximal portion of the loop support member; and a protrusion affixed to an interior surface of the cylindrical member dimensioned and positioned to be slidable within the slot and to snare the exposed length of suture material, the protrusion positioned proximal of the slot when the snaring means is in the loading position and distal of the loop support member proximal end when the snaring means is in the deployed position.

5. The device recited in claim 4, wherein the guiding means comprises a second longitudinal bore extending from the groove to the loop support member proximal end, the second bore dimensioned to permit a passage of suture material therethrough.

6. A device for delivering a loop of suture material for endoscopic ligation, the suture material having a free end and a slip knot therein for tightening the loop, the device comprising:

an outer tube having a longitudinal bore extending from a distal end to a proximal end;

an impelling member having a distal portion dimensioned to freely slide within the outer tube bore and a longitudinal bore extending from a distal end to a proximal end, the impelling member longitudinally slidable relative to the outer tube between a loading position and a deployed position distal of the loading position;

a loop support member having:

a proximal portion dimensioned to reside at least partially within the outer tube bore and having a proximal section dimensioned to reside at least partially within the impelling member bore, the proximal section having an exterior;

a longitudinal bore extending from a loop support member distal end to a loop support member proximal end;

means for releasably retaining the loop of suture material circumferentially thereon, the loop thereby encircling the loop support member bore;

means for preventing a proximal movement of the slip knot beyond the loop retaining means;

means for affixing the free end of suture material to the loop support member;

means for making accessible to the exterior of the loop support member proximal section an exposed length of suture material between the free end and the slip knot; and means for mating the loop support member with the outer tube generally adjacent the outer tube distal end; and means positioned on an interior surface of the impelling member for snaring the exposed length of suture material when the impelling member is moved from the loading position to the deployed position, the snaring means for pulling the snared exposed length of suture material against the slip knot and thereby tightening the loop when the impelling member is moved into the deployed position.

7. The suture loop delivery device recited in claim 6, further comprising:

a first grasping member affixed adjacent the outer tube proximal end; and a second grasping member affixed adjacent the impelling member proximal end;

the first and the second grasping members for facilitating sliding the impelling member relative to the outer tube and thereby facilitating a deploying of the device.

8. The suture loop delivery device recited in claim 6, further comprising limiting means for limiting the longitudinal sliding of the impelling member relative to the outer tube.

9. The suture loop delivery device recited in claim 8, wherein the loop retaining means comprises a circumferential groove in surrounding relation to the loop support member bore adjacent the loop support member distal end, the groove adapted to hold the loop and the slip knot thereon when the loop is not subject to tension and to permit the loop and slip knot to slide theroff when tension is applied thereto.

10. The suture loop delivery device recited in claim 9, wherein the loop support member bore comprises a first bore and the loop support member further has a second bore generally parallel to the first bore extending from the proximal end to the distal end and dimensioned to permit suture material to pass therethrough and to block a passage of the slip knot therethrough, the free end of the suture material threadable through the second bore from the groove to the loop support member proximal end.

11. The suture loop delivery device recited in claim 10, wherein:

the loop support member further has a slot therein adjacent the proximal end and adjacent the second bore, the second bore on a first side of the slot;

the means for affixing the suture material free end comprises means for affixing the suture material free end adjacent a second side of the slot; and when in use the suture material free end emerging from the second bore proximal end is affixed so as to cross the slot from the slot first side to the slot second side, thereby exposing a length of suture material to the exterior of the loop support member.

12. The suture loop delivery device recited in claim 11, wherein the snaring means comprises a pin means affixed to the impelling member interior surface and axially positioned to engage the exposed section of suture material when the impelling member is in the loading position, and further comprising means for radially aligning the impelling member and the outer tube to position the pin means adjacent the notch when the impelling means is in the loading position, thereby permitting the pin to snare the exposed section of suture material.

13. The suture loop delivery device recited in claim 12, wherein:

the loop support member has a wider distal portion, a narrower proximal portion, and a shoulder between the distal portion and the proximal portion, the shoulder having a notch therein, the notch insufficiently deep to communicate with the loop support member bore, the loop support member further having a dimple within the notch; and the outer tube distal end has a tab protruding therefrom, the tab dimensioned to fit within the notch, the tab further having an inwardly facing protrusion thereon dimensioned and adapted to snap fit into the dimple.

14. The suture loop delivery device recited in claim 6, wherein the impelling member bore is dimensioned to permit a grasping tool to pass therethrough, wherein the grasping tool is usable to grasp a piece of tissue to be ligated prior to the impelling member being moved into the deployed position to ligate the grasped piece of tissue.

15. The suture loop delivery device recited in claim 6, further comprising means, in communication with the loop support member, for cutting the suture material between the slip knot and the free end, the cutting means having a cutting edge movable between a first position in spaced relation to the suture material and a second position in cutting relation to the suture material between the slip knot and the free end.

16. A device for delivering a loop of suture material for endoscopic ligation, the suture material having a free end and a slip knot therein for permitting the loop to be tightened, the device comprising:

an outer tube having a longitudinal bore extending from a distal end to a proximal end and means for affixing the free end of suture material adjacent the proximal end;

an impelling member having:
a distal portion dimensioned to freely slide within the outer tube bore;
a longitudinal bore extending from a distal end to a proximal end; and
means positioned adjacent the distal end for releasably retaining the loop of suture material circumferentially thereon, the loop thereby encircling the impelling member bore;

means for preventing a proximal movement of the slip knot beyond the loop retaining means;

the impelling member, having a loop of suture material retained thereon, is positionable within the outer tube bore;

the free end of suture material is threadable proximalward from the impelling member distal end, through the impelling member bore, to the outer tube proximal end, whereon it is affixable; and the device is deployable by pushing the impelling member in a distal direction relative to the outer tube, pulling the free end of suture material against the slip knot and thereby tightening the loop.

17. A method of delivering a loop of suture material for endoscopic ligation, the suture material having a free end and a slip knot therein for permitting the loop to be tightened, the method comprising the steps of:

providing a loop delivery device comprising:
an outer tube having a length and a longitudinal bore extending from a distal end to a proximal end;
an impelling member having a distal portion dimensioned to freely slide within the outer tube bore and having a distal end and a proximal end; and
a generally cylindrical loop support member having a proximal portion dimensioned to reside at least partially within the outer tube bore and having a longitudinal bore extending from a distal end to a proximal end;

retaining the loop of suture material circumferentially adjacent the distal end of the loop support member, the loop thereby encircling the loop support member bore;

preventing a proximal movement of the slip knot beyond a position generally adjacent the distal end of the loop support member bore;

affixing the free end of suture material to the loop support member;

exposing a length of suture material between the free end and the slip knot to an exterior of the loop support member;

positioning the impelling member within the outer tube;

mating the loop support member with the impelling member generally adjacent the impelling member distal end;

positioning the loop support member within the outer tube bore;

snaring the exterior section of suture material within the outer tube bore;

deploying the device by pushing the impelling member in a distal direction relative to the outer tube, pulling the snared exterior section of suture material against the slip knot and thereby tightening the loop.

18. A method of delivering a loop of suture material for endoscopic ligation, the suture material having a free end and a slip knot therein for permitting the loop to be tightened, the method comprising the steps of:

providing a loop delivery device comprising:
an outer tube having a length and a longitudinal bore extending from a distal end to a proximal end;
an impelling member having a distal portion dimensioned to freely slide within the outer tube bore and having a distal end and a proximal end; and
a generally cylindrical loop support member having a proximal portion dimensioned to reside at least partially within the outer tube bore and having a longitudinal bore extending from a distal end to a proximal end;

retaining the loop of suture material circumferentially adjacent the distal end of the loop support member, the loop thereby encircling the loop support member bore;

preventing a proximal movement of the slip knot beyond a position generally adjacent the distal end of the loop support member bore;

affixing the free end of suture material to the loop support member;

making accessible to an exterior of the loop support member a section of suture material between the free end and the slip knot;

positioning the impelling member within the outer tube;

mating the loop support member with the impelling member generally adjacent the impelling member distal end;

positioning the loop support member within the outer tube bore;

snaring the exterior section of suture material within the outer tube bore;

passing a grasping tool in a distal direction through the impelling member bore and loop support member bore, the grasping tool having actuating means at a proximal end and grasping means at a distal end;

grasping a piece of tissue to be ligated with the grasping tool;

deploying the device by pushing the impelling member in a distal direction relative to the outer tube, pulling the snared exterior section of suture material against the slip knot and thereby tightening the loop and ligating the grasped tissue.

* * * * *